US00PP29420P2

(12) United States Plant Patent
Egger

(10) Patent No.: US PP29,420 P2
(45) Date of Patent: Jun. 19, 2018

(54) ***HEUCHERA* PLANT NAMED 'TNHEUNER'**

(50) Latin Name: ***Heuchera* hybrid**
Varietal Denomination: TNHEUNER

(71) Applicant: Terra Nova Nurseries, Inc., Canby, OR (US)

(72) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 45 days.

(21) Appl. No.: 15/530,252

(22) Filed: Dec. 13, 2016

(51) Int. Cl.
*A01H 5/12* (2018.01)
*A01H 5/02* (2018.01)

(52) U.S. Cl.
USPC ..... Plt./440
CPC ..... *A01H 5/02* (2013.01); *A01H 5/12* (2013.01)

(58) Field of Classification Search
USPC ..... Plt./440
See application file for complete search history.

*Primary Examiner* — Anne Marie Grunberg
(74) *Attorney, Agent, or Firm* — Klarquist Sparkman, LLP

(57) ABSTRACT

A new and distinct *Heuchera* plant characterized by dark red to burgundy colored leaves, medium size, slightly lobed, geranium-like leaves, yellow green flowers in short spikes in spring, good sun tolerance, a medium large, mounding habit with excellent crown count, and excellent vigor.

1 Drawing Sheet

Botanical denomination: *Heuchera* hybrid.
Variety designation: 'TNHEUNER'.

BACKGROUND OF THE INVENTION

The present invention relates to a new and distinct cultivar of *Heuchera* and given the cultivar name of 'TNHEUNER'. *Heuchera* is in the family Saxifragaceae. *Heuchera* 'TNHEUNER' originated as a controlled cross using *Heuchera* 'K797-3', a proprietary, unpatented, unnamed plant as the seed parent, and *Heuchera* 'K994-1', a proprietary, unpatented, unnamed plant as the pollen parent. These parents are a result of breeding using hardy *Heuchera richardsonii* with proprietary hybrid lines. *Heuchera* 'TNHEUNER' was bred to be a hardy, large, landscape plant.

Compared to the seed parent, *Heuchera* 'K797-3', the new cultivar has a dark red to burgundy rather than brown leaves and gold rather than light pink flowers.

Compared to the pollen parent, *Heuchera* 'K994-1', the new cultivar has a larger habit.

Compared to *Heuchera* 'Cherry Cola', U.S. Plant Pat. No. 22,967, the new cultivar has a larger habit and larger leaves. The foliage of the new cultivar is dark red to burgundy colored rather than soft red. The flowers of the new cultivar are yellow green rather than rust red.

Compared to *Heuchera* 'Root Beer', U.S. Plant Pat. No. 23,173, the new cultivar has a larger habit and leaves. The foliage of the new cultivar is more intensely colored and less lobed.

This new *Heuchera* is uniquely distinguished by:

1. dark red to burgundy colored leaves,
2. medium size, slightly lobed, geranium-like leaves,
3. yellow green flowers in short spikes in spring,
4. good sun tolerance, 5. a medium large, mounding habit with excellent crown count, and
6. excellent vigor.

This new cultivar has been reproduced only by asexual propagation (tip cuttings and tissue culture using growing tips). Each of the progeny exhibits identical characteristics to the original plant. Asexual propagation in 2013 by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWINGS

FIG. 1 shows one-year-old plants of *Heuchera* 'TNHEUNER' growing in the trial bed in October in Canby, Oreg.

FIG. 2 shows the same plants in flower the next April.

DETAILED PLANT DESCRIPTION

The following is a detailed description of the new *Heuchera* cultivar based on observations taken in April of one-year-old specimens growing in the trial field in June in Canby, Oreg. Canby is Zone 8 on the USDA Hardiness map. Temperatures range from a high of 95° F. in August to an average of 32° F. in January. Normal rainfall in Canby is 42.8 inches per year. The color descriptions are all based on *The Royal Horticultural Society Colour Chart*, 5$^{th}$ edition, 2007.

Plant:

*Form.*—Basal rosette, herbaceous perennial.

*Hardiness.*—USDA Zone 4 to 9.

*Size.*—20 cm tall from top of the foliage to the ground and 40 cm wide.

*Number of crowns*.—About 20.
*Habit*.—Medium, mounding.
*Vigor*.—Excellent.

Leaf:
*Type*.—Simple.
*Arrangement*.—Rosette.
*Shape*.—Broadly ovate to orbicular.
*Number*.—About 200.
*Blade size*.—Grows to 14 cm long and 12 cm wide.
*Venation*.—Palmate.
*Lobing/division*.—7 shallow palmate lobes.
*Margins*.—Crenate, slightly undulate.
*Apex*.—Mucronulate.
*Base*.—Cordate, strongly overlapping and often spiraling in.
*Surface texture*.—Glandular-puberulent on both sides.
*Leaf rugosity*.—Absent.
*Petiole description*.—Grows to 19 cm long and 3.5 mm wide, glandular hairs, Greyed Purple 187B.
*Leaf color*.—New leaves, top side Greyed Red 178B with veins 181C, bottom side closest to Red Purple 59A with veins 59D; mature leaves late spring leaves topside Greyed Purple 187B, veins 187D, bottom side closest to Red Purple 59A with veins 59D.

Inflorescence:
*Size*.—Grows to 12 cm wide and 27 cm long.
*Type*.—Upright and side growing thyrse.
*Number of flowers per thyrse*.—About 180.
*Number of thyrse*.—About 20.
*Peduncle*.—Grows to 35 cm long and 3 mm wide at base, glandular hairs, Greyed Purple 187B.
*Pedicel*.—Grows to 8 mm long, with glandular hairs, Greyed Purple 187B.
*Bloom period*.—Late May to June in Canby, Oreg.

Flower bud:
*Size*.—3 mm wide and 4 mm long.
*Description*.—Glandular puberulent, ovoid, down facing.
*Color*.—Greyed Orange 173B.

Flower:
*Type*.—Perfect.
*Shape*.—Campanulate.
*Attitude*.—Side-facing.
*Size*.—5 mm long and 3.5 mm wide.
*Corolla description*.—5 petals, each 2.5 mm long and 1 mm wide, spatulate, margins entire, tip acute, glandular-puberulent on both sides, both sides Greyed Yellow 160D with back side tinted Greyed Orange 173B.
*Calyx description*.—Campanulate, 5 mm long and 4 mm wide, with 5 lobes with wide sinuses divided ½ way to the base, each 2 mm wide and 2.5 mm long, oblong in shape, back side glandular-puberulent with glandular hairs (Greyed Orange 173B), glabrous inside, tip obtuse, margin entire, both sides Green Yellow 1D, tinted Greyed Orange 173B on back side, strongest at base.
*Stamen description*.—5 in number, filaments 1.5 mm long, Yellow Green 155C, anthers 0.5 mm long, Yellow Green 155C, pollen none.
*Pistil description*.—1, 2-beaked, 5 mm long and 2 mm wide, Yellow Green 155C overall, ovary 2 mm long and 2 mm wide, style 2 mm long.
*Fragrance*.—None.
*Lastingness*.—Each thyrse blooms for about 3 weeks on the plant.

Fruit and seed: None seen.

Pest and disease tolerance: The new cultivar is typical to the genus. No known resistances to pests or diseases. No problems have been found in Canby, Oreg.

I claim:

1. A new and distinct *Heuchera* plant as herein illustrated and described.

* * * * *

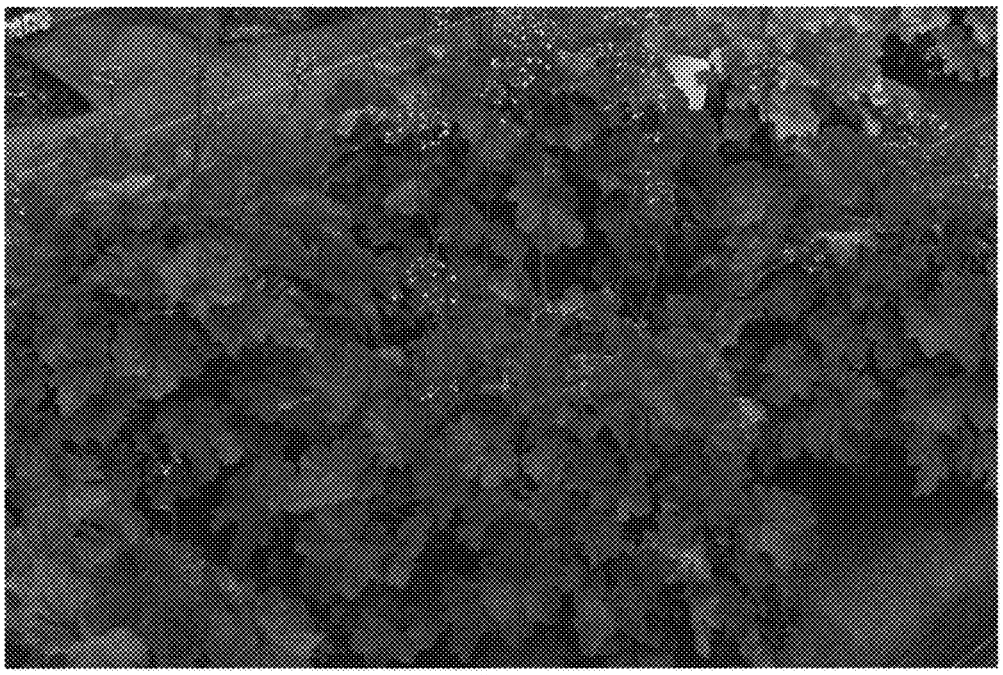

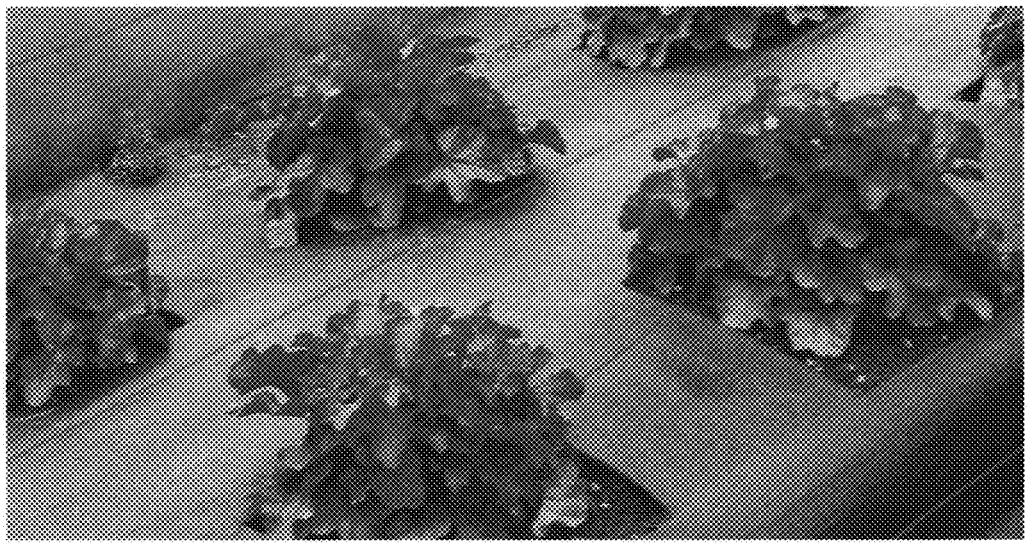
FIG. 1 above, FIG. 2 below